US011619575B2

(12) United States Patent
Kim et al.

(10) Patent No.: US 11,619,575 B2
(45) Date of Patent: Apr. 4, 2023

(54) METHOD OF DETECTING CANCER CELLS USING MICRO-VIBRATION

(71) Applicant: Ewha University-Industry Collaboration Foundation, Seoul (KR)

(72) Inventors: Minsuk Kim, Seoul (KR); Hyue Yun Kim, Seoul (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 720 days.

(21) Appl. No.: 16/655,391

(22) Filed: Oct. 17, 2019

(65) Prior Publication Data

US 2020/0300747 A1    Sep. 24, 2020

(30) Foreign Application Priority Data

Mar. 21, 2019   (KR) .................... 10-2019-0032587
Jun. 7, 2019    (WO) ............... PCT/KR2019/006892

(51) Int. Cl.
*G01N 15/14*    (2006.01)
*G01N 21/88*    (2006.01)
(Continued)

(52) U.S. Cl.
CPC ....... *G01N 15/147* (2013.01); *G01N 15/1436* (2013.01); *G01N 21/8851* (2013.01); *G06T 7/20* (2013.01); *G16H 30/00* (2018.01); *G01N 2015/0003* (2013.01); *G01N 2015/0065* (2013.01); *G01N 2015/1075* (2013.01); *G01N 2015/1495* (2013.01); *G01N 2021/889* (2013.01)

(58) Field of Classification Search
CPC ............ G01N 15/147; G01N 15/1475; G01N 15/1436; G01N 21/8851; G01N 2015/1006; G01N 2015/0065; G01N 2015/1075; G01N 2015/0003; G01N 2015/1495; G16H 30/00; G06T 7/20; G06T 7/0016; G06T 2207/30024; G06T 2207/10016
See application file for complete search history.

(56) References Cited

U.S. PATENT DOCUMENTS 5,620,854 A * 4/1997 Holzrichter .......... C12Q 1/6869
                                                    435/7.1
6,153,113 A * 11/2000 Goodrich ............... B01D 21/26
                                                    436/523
(Continued)

FOREIGN PATENT DOCUMENTS

CN      201840643 U   *  5/2011
JP      2009-063565      3/2009
(Continued)

OTHER PUBLICATIONS

Sultan L Nelson et al., "Vibrational Profiling of Brain Tumors and Cells", Theranostics, 7, pp. 2417-2430, 2017.
(Continued)

*Primary Examiner* — Sang H Nguyen
(74) *Attorney, Agent, or Firm* — Lex IP Meister, PLLC

(57) ABSTRACT

The present invention relates to a method for cancer cell separation, and more specifically, relates to a method for cancer cell separation using micro-vibration.

19 Claims, 11 Drawing Sheets
(11 of 11 Drawing Sheet(s) Filed in Color)

(51) Int. Cl.
*G06T 7/20* (2017.01)
*G16H 30/00* (2018.01)
*G01N 15/00* (2006.01)
*G01N 15/10* (2006.01)

(56) References Cited

U.S. PATENT DOCUMENTS

| | | | |
|---|---|---|---|
| 2004/0191906 A1* | 9/2004 | Holzer | C12M 35/04 |
| | | | 435/383 |
| 2014/0339088 A1* | 11/2014 | Schmelz | B03C 5/026 |
| | | | 204/547 |
| 2014/0367260 A1* | 12/2014 | Dickerson | B03C 5/028 |
| | | | 204/547 |
| 2017/0153237 A1 | 6/2017 | Yu et al. | |
| 2020/0206740 A1* | 7/2020 | Chiu | B01L 3/50273 |

FOREIGN PATENT DOCUMENTS

| | | |
|---|---|---|
| KR | 10-2009-0095209 | 9/2009 |
| KR | 10-2016-0091180 | 8/2016 |
| WO | 2017-195794 | 11/2017 |
| WO | 2018-223132 | 12/2018 |

OTHER PUBLICATIONS

Neal Wadhwa et al., "Motion microscopy for visualizing and quantifying small motions", PNAS, 114, pp. 11639-11644, Oct. 31, 2017.

Wadhwa, Neal et al., "Motion microscopy for visualizing and quantifying small motions", PNAS, 2017, 114(44), p. 11639-11644.

Sun, Hongyue et al., "Visualization of fast-moving cells in vivo using digital holographic video microscopy", Journal of Biomedical Optics, 2008, 13(1), 014007, p. 1-9.

Menon, Shalini et al., "Cancer cell invasion is enhanced by applied mechanical stimulation", PLoS ONE, 2011, 6(2), e17277, p. 1-11.

Fraldi, M. et al., "A frequency-based hypothesis for mechanically targeting and selectively attacking cancer cells", Journal of The Royal Society Interface, 2015, 12, 20150656, p. 1-16.

KIPO, International Search Report and Written Opinion of PCT/KR2019/006892 dated Dec. 23, 2019.

* cited by examiner

[FIG. 1a]
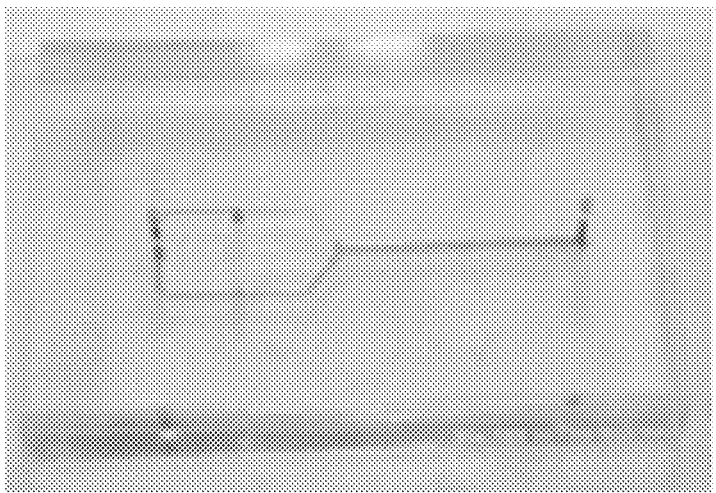
[FIG. 1b]

[FIG. 1c]
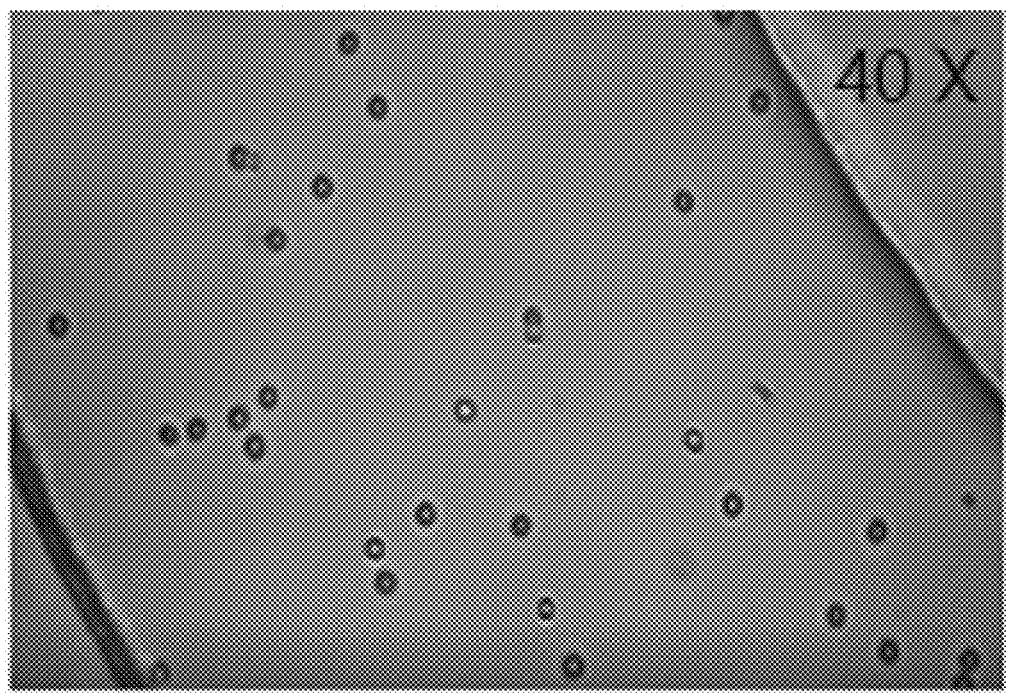

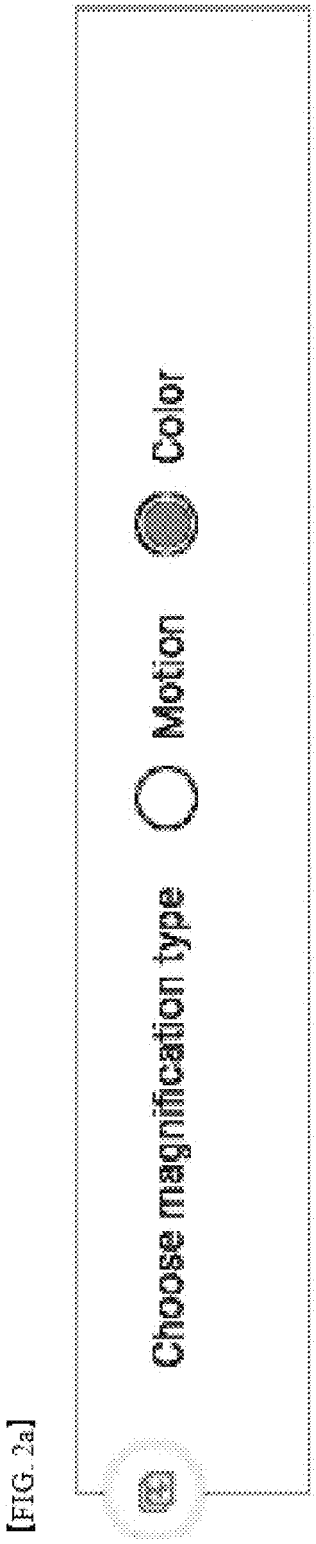
[FIG. 2a]

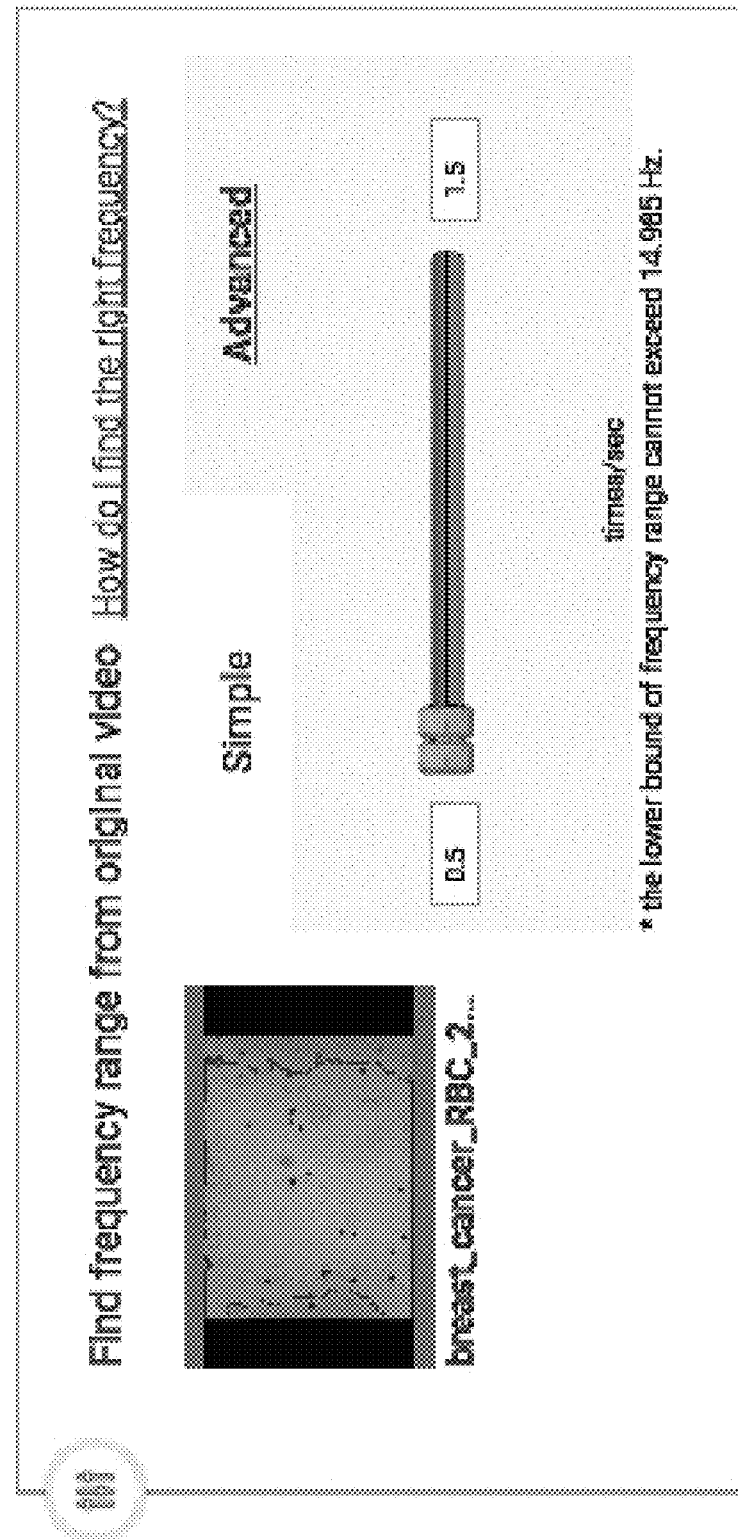
[FIG. 2b]

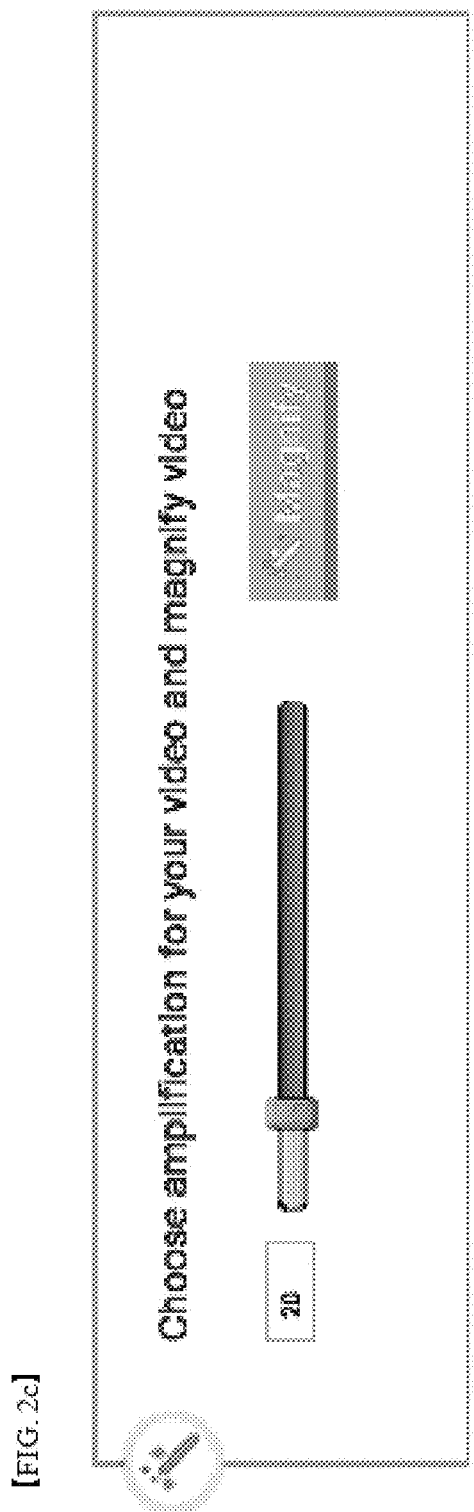
[FIG. 2c]

[FIG. 3]
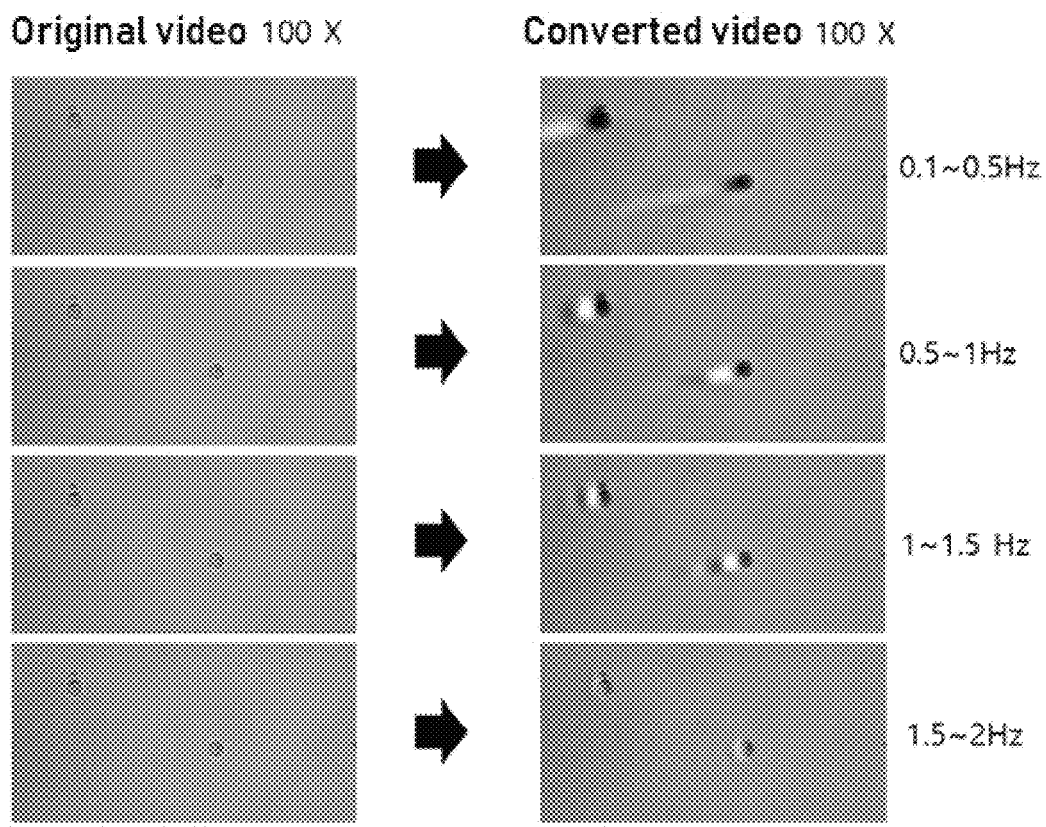

[FIG. 4a]
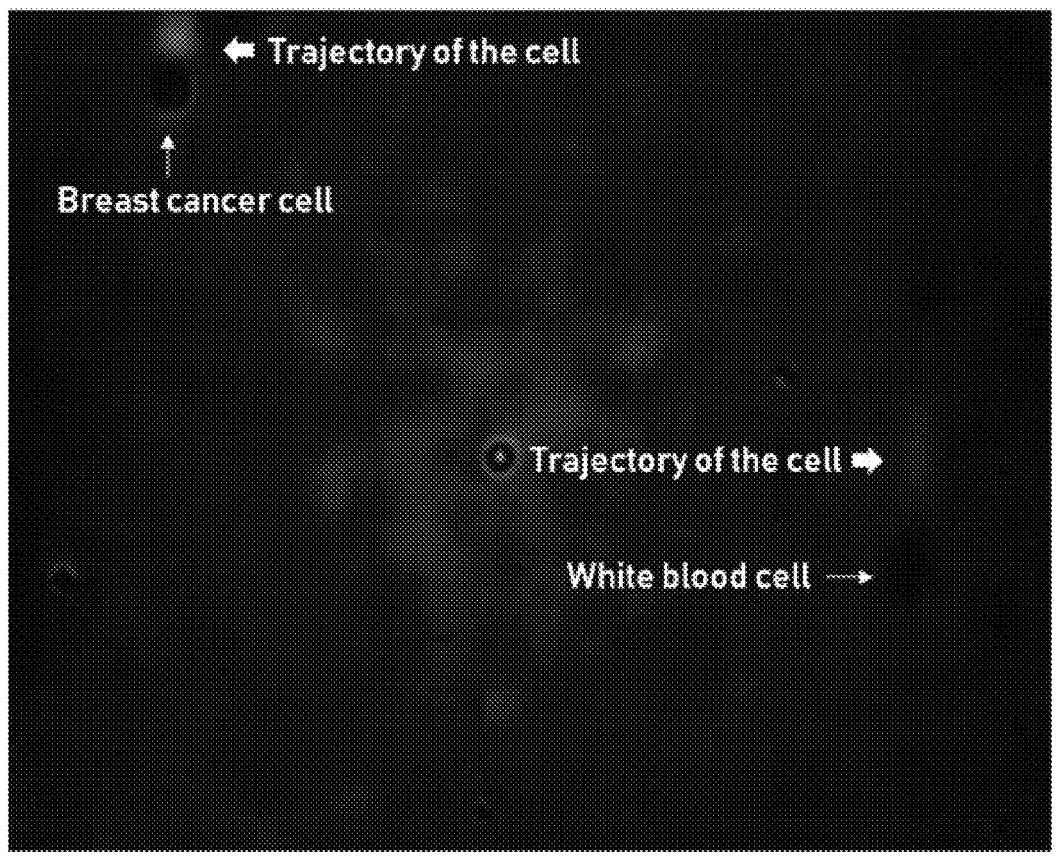

[FIG. 4b]
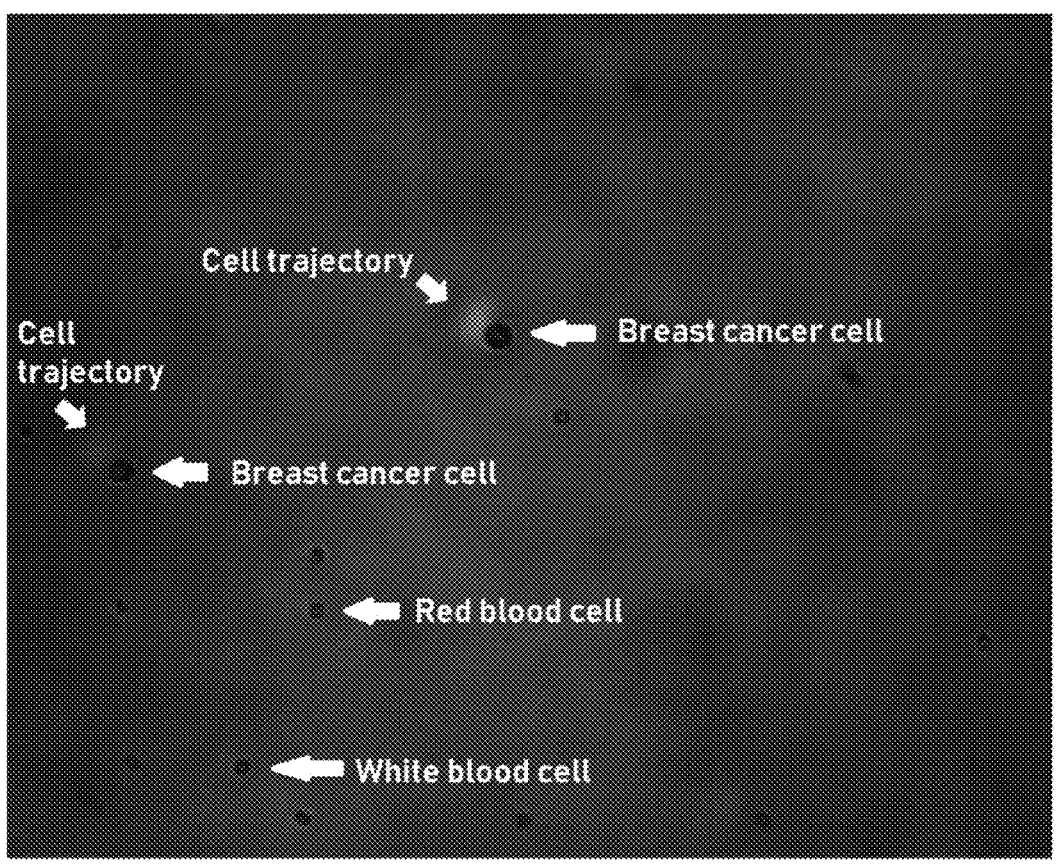

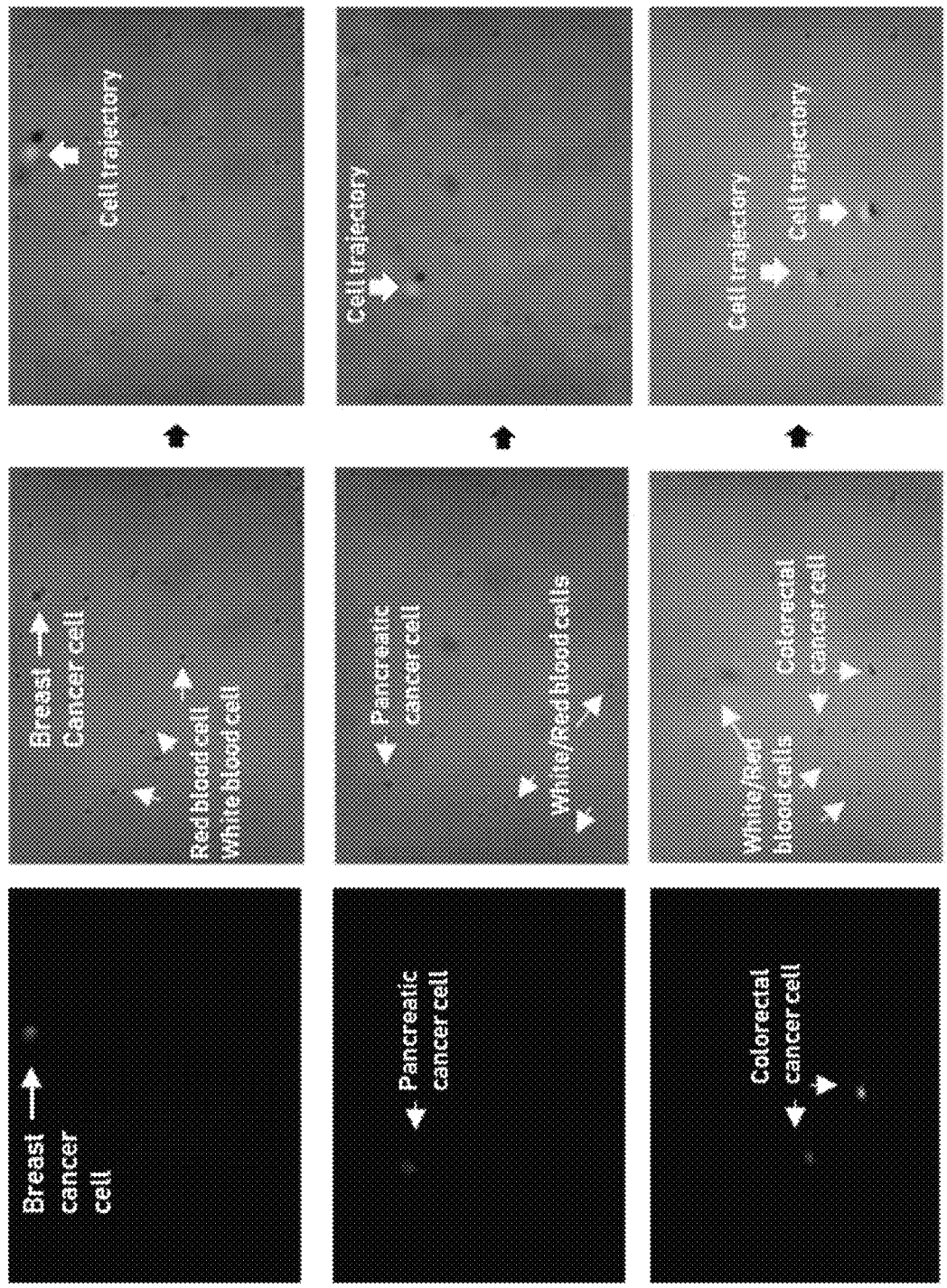
[FIG. 5]

[FIG. 6a]
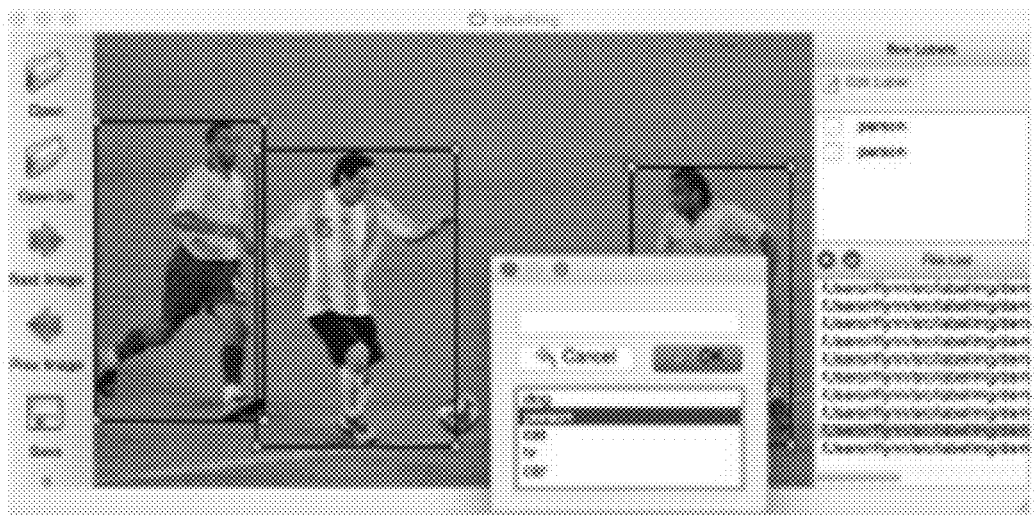
[FIG. 6b]
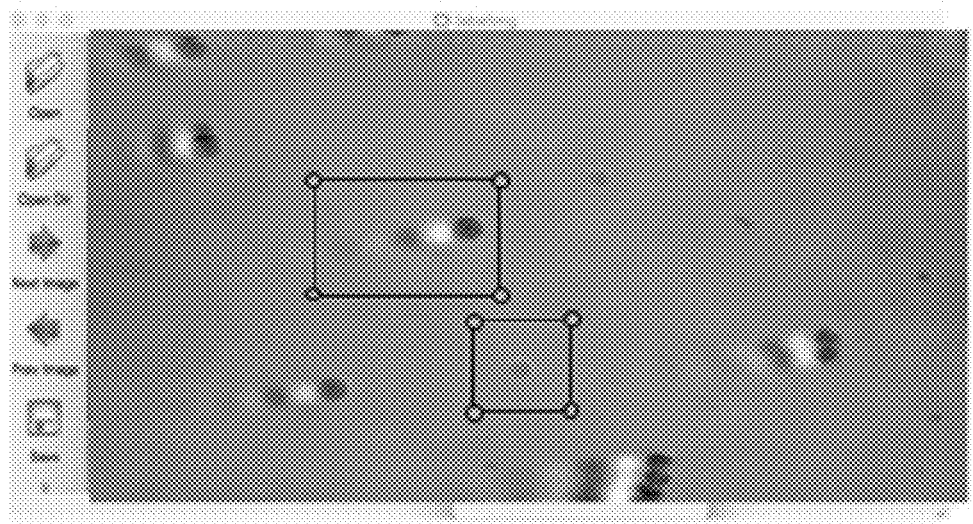

[FIG. 6c]
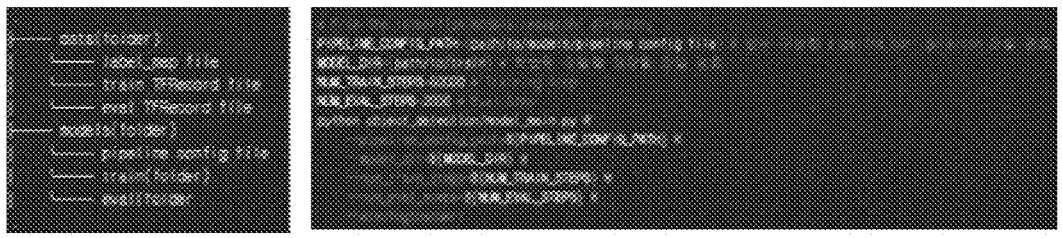
[FIG. 6d]
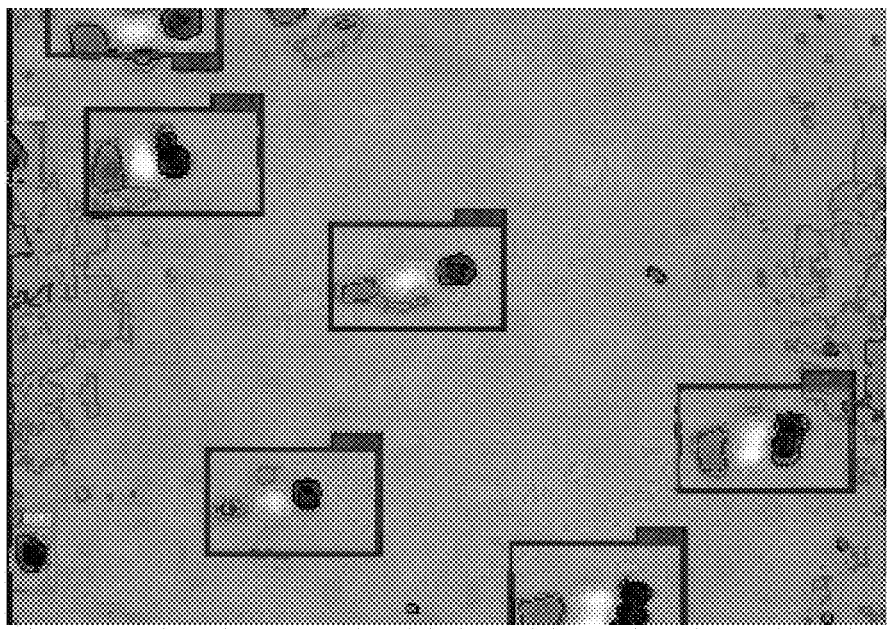

METHOD OF DETECTING CANCER CELLS USING MICRO-VIBRATION

TECHNICAL FIELD

The present invention relates to a method for detecting cancer cells by separating them from normal cells, and more specifically, relates to a method for detecting cancer cells by amplifying movement of cancer cells in a specific frequency range, and distinguish the cancer cells from normal cells using movement of cancer cells.

RELATED ART

As a method for detecting cancer cells, methods using MRI and X-ray and the like are known, and a method for diagnosing cancer by detecting a gene or protein expressed from the gene. In particular, as a visualization method for distinguishing cancer cells, there are a method using an enzyme, fluorescence, and the like.

However, while the human visual system is excellent at recognizing and interpreting motions, the sensitivity to recognizable motions is limited and motions less than a certain threshold cannot be detected by human visual system. It is difficult to visualize these motions which are less than a certain threshold, but these small motions which are less than a certain threshold are important, and for example, they may act very importantly in identifying physical mechanisms or mechanical defects, and the like. The invention of the microscope has made it possible to visualize small static physical properties less than the threshold, but it has been very difficult to visualize small dynamic motions less than the threshold.

Meanwhile, there is a micro-vibration technology of cells using a laser, but it is an uneasy method that should bring a micro-vibration sensor close to cells to perform an experiment, and needs expensive experiment equipment and has technical difficulties.

DISCLOSURE

Technical Problem

An embodiment of the present invention relates to a method for cancer cell detection, for determining cancer cells using micro-vibration of cells.

Another embodiment of the present invention relates to a method for providing information for cancer diagnosis using micro-vibration of cells.

Other embodiment of the present invention relates to a method for providing information for predicting responses or prognosis for cancer treatment using micro-vibration of cells.

Technical Solution

The present inventors have completed the present invention by confirming that it is possible to distinguish normal cells and cancer cells, by applying a motion microscope which amplifies small dynamic motions less than a threshold recorded in an image at a cell level.

According to one embodiment of the present invention, it relates to a method of detecting cancer cells, comprising steps of preparing video of cells moving in a liquid medium and visualizing micro-vibration of the cells by amplifying the video in a specific frequency range.

The method of detecting cancer cells may further comprise a step of determining cells having a motion trajectory among the visualized cells as cancer cells.

The motion trajectory is a motion of the liquid medium occurring due to the motion of cells, and it may be visualized by the amplifying. The motion trajectory may be a pixel of which brightness value is changed, or a set of pixels of which brightness value is changed, when compared pixels at the same position at the same random moment, in the video of the moving cells, and for example, may be a pixel with an increasing brightness value, a set of pixels with an increasing brightness value, a pixel with an increasing level of brightness, or a set of pixels with an increasing level of brightness, and the motion trajectory may move together according to the movement of the cells.

The step of determining may determine the cells suspected of having cancer as cancer cells, when the change in brightness value of the trajectory generated after the frequency amplification of the cells suspected of having cancer is larger than the change of the brightness value of the trajectory generated after the frequency amplification of the normal cells.

The cancer cell may be one or more kinds selected from the group consisting of breast cancer cells, colorectal cancer cells, pancreatic cancer cells, ovarian cancer cells, liver cancer cells, brain cancer cells, prostate cancer cells, lung cancer cells, gastric cancer cells, skin cancer cells, oral cancer cells, rectal cancer cells, laryngeal cancer cells, thyroid cancer cells, parathyroid cancer cells, colon cancer cells, bladder cancer cells, peritoneal carcinoma cells, adrenal cancer cells, tongue cancer cells, small intestine cancer cells, esophageal cancer cells, renal pelvis cancer cells, renal cancer cells, heart cancer cells, duodenal cancer cells, ureteral cancer cells, urethral cancer cells, pharynx cancer cells, vaginal cancer cells, tonsil cancer cells, anal cancer cells, pleura cancer cells, thymic carcinoma cells, nasopharynx cancer cells, and cancer stem cells.

The frequency range may be 0.1 to 1.5 Hz.

The liquid medium may be set to have specific velocity for the cells in the liquid medium to have the velocity of 10 to 30 um/s.

The flow velocity of the medium may be 10 to 30 um/s.

The amplifying the video in a specific frequency range may be performed by a motion microscope.

The micro-vibration of the cells may be amplified by 10 to 30 times.

The liquid medium may be a biological liquid medium.

The biological medium may be one or more kinds selected from the group consisting of blood, plasma, serum, body fluid, urine, mucus, saliva, lymph fluid, respiratory secretion, spinal fluid, brain spinal fluid, phlegm, sweat, vaginal mucus, sperm, amniotic fluid, amnion fluid, synovia, tissue lavage fluid, tears and nasal mucus.

The blood may be diluted with saline in a volume ratio of more than 1 to 100 times.

The biological liquid medium may be separated from a subject.

The subject may be one or more kinds selected from the group consisting of rodents, mice, rats, hamsters, guinea pigs, reptiles, amphibians, mammals, dogs, cats, pigs, cattle, sheep, monkeys, primates, mammals other than humans, primates other than humans and humans.

The subject may be a subject suspected of suffering from a cancer, a cancer patient subject, or a subject being treated a cancer treatment. Accordingly, by applying the method according to one embodiment of the present invention, information for cancer diagnosis may be provided by detecting cancer cells in a subject suspected of suffering from a cancer, or information such as progress or prognosis of cancer, and efficacy monitoring of anticancer treatment and the like may be provided using a sample obtained from a cancer patient or a subject being treated a cancer treatment.

According to another embodiment of the present invention, it relates to a method of providing information for cancer diagnosis, comprising visualizing micro-vibration of cells by amplifying a video of cells moving in a liquid medium in a specific frequency range, and detecting cancer cells having a motion trajectory.

According to other embodiment of the present invention, it relates to a method of providing information for cancer diagnosis, comprising a step of detecting cells in which motion trajectory of cells in a liquid medium by frequency amplification occurs.

According to other embodiment of the present invention, it relates to a method of providing information for predicting responses or prognosis for cancer treatment, comprising a step of visualizing micro-vibration of cells by amplifying frequency in a video of cells moving in a biological liquid sample, separated from a subject being treated a cancer treatment, to detect cancer cells having a cell motion trajectory.

According to other embodiment of the present invention, it relates to a method of providing information for predicting responses or prognosis for cancer treatment, comprising a step of detecting cells in which a motion trajectory of cells in a liquid medium by frequency amplification occurs, in a biological sample separated from a subject being treated a cancer treatment.

According to other embodiment of the present invention, it relates to a method of visualizing cancer cell micro-vibration, comprising a step of visualizing micro-vibration of the cancer cells by amplifying frequency in a video of cells moving in a liquid medium.

According to other embodiment of the present invention, it relates to a method of determining cancer cells in a sample, comprising steps of preparing a biological sample; applying fluidity to the biological sample; filming the biological sample in which the fluidity is applied; amplifying the frequency of the filmed video; and analyzing the amplified video to determine cancer cells.

According to other embodiment of the present invention, it relates to a method of providing information for cancer diagnosis, comprising steps of preparing a biological sample separated from a subject suspected of having cancer; applying fluidity to the biological sample; filming the biological sample in which the fluidity is applied; amplifying the frequency of the filmed video; and analyzing the amplified video to determine cancer cells.

According to other embodiment of the present invention, it relates to a method of providing information for predicting responses or prognosis for cancer treatment, comprising steps of preparing a biological sample separated from a subject being treated a cancer treatment; applying fluidity to the biological sample; filming the biological sample in which the fluidity is applied; and amplifying the frequency of the filmed video.

According to other embodiment of the present invention, it relates to a detection device of cancer cells in a sample, comprising a flow device which applies fluidity to a biological sample; a filming device which films the biological sample; and an amplification device which amplifies the frequency of the filmed video.

The detection device of cancer cells in a sample may further comprise a determination device which determines cancer cells by analyzing the amplified video.

According to other embodiment of the present invention, it relates to a cancer cell detection system, comprising an amplifying unit for amplifying a video of cells moving in a liquid medium in a specific frequency range; and a detecting unit for detecting cancer cells by analyzing the video amplified by the amplifying unit.

The detecting unit may detect cells in which a motion trajectory occurs by the amplification as cancer cells.

Hereinafter, the present invention will be described in more detail.

Herein, the term "liquid medium" means a medium in a liquid state, and includes all that fluidity is applied to enable cells to move by velocity. For example, it may be a liquid sample, a biological liquid medium, or a biological liquid sample, such as water, sodium chloride aqueous solution, saline, physiological saline, buffer physiological saline, PBS (phosphate buffer saline), and the like. The biological liquid medium may be one or more kinds selected from the group consisting of blood, plasma, serum, body fluid, urine, mucus, saliva, lymph fluid, respiratory secretion, spinal fluid, brain spinal fluid, phlegm, sweat, vaginal mucus, sperm, amniotic fluid, amnion fluid, synovia, tissue lavage fluid, tears and nasal mucus, but not limited thereto.

The biological liquid medium may be separated from a subject. For example, the subject may be a subject suspicious of having cancer or a subject being treated an anti-cancer treatment.

Herein, the term "biological sample" includes body fluid, saliva, tissue, organ, and the like, and for example, may be one or more kinds selected from the group consisting of blood, plasma, serum, body fluid, urine, mucus, saliva, lymph fluid, respiratory secretion, spinal fluid, brain spinal fluid, phlegm, sweat, vaginal mucus, sperm, amniotic fluid, amnion fluid, synovia, tissue lavage fluid, tears and nasal mucus, but not limited thereto.

The liquid medium or biological sample may be used as diluted. For example, it may be used as diluted in a volume ratio of over 1 time to 100 times, over 1 time to 90 times, over 1 time to 80 times, over 1 time to 70 times, over 1 time to 60 times, over 1 time to 50 times, over 1 time to 40 times, over 1 time to 35 times, 10 times to 100 times, 10 times to 90 times, 10 times to 80 times, 10 times to 70 times, 10 times to 60 times, 10 times to 50 times, 10 times to 40 times, 10 times to 35 times, 20 times to 100 times, 20 times to 90 times, 20 times to 80 times, 20 times to 70 times, 20 times to 60 times, 20 times to 50 times, 20 times to 40 times, 20 times to 35 times, 30 times to 100 times, 30 times to 90 times, 30 times to 80 times, 30 times to 70 times, 30 times to 60 times, 30 times to 50 times, 30 times to 40 times, or 30 times to 35 times, and for example, the liquid medium or biological sample may be used as diluted in the above volume ratio with water, sodium chloride aqueous solution, saline, physiological saline, buffer physiological saline, PBS and the like, but not limited thereto.

Herein, the term "subject", "object", "target" and "patient" and the like include mammals, primates, humans, mammals other than humans, primates other than humans, rodents, mice, rats, hamsters, guinea pigs, reptiles, amphibians, pigs, cows, sheep, monkeys, Canidae, Felidae, lagomorph, and the like, but not limited thereto. In one example of the present invention, a subject of interest is a human. The subject may be a subject suspected of having cancer, and for example, the subject may be a subject suspected of having breast cancer cells, colorectal cancer cells, pancreatic cancer cells, ovarian cancer cells, liver cancer cells, brain cancer cells, prostate cancer cells, lung cancer cells, gastric cancer cells, skin cancer cells, oral cancer cells, rectal cancer cells, laryngeal cancer cells, thyroid cancer cells, parathyroid cancer cells, colon cancer cells, bladder cancer cells, peritoneal carcinoma cells, adrenal cancer cells, tongue cancer cells, small intestine cancer cells, esophageal cancer cells, renal pelvis cancer cells, renal cancer cells, heart cancer cells, duodenal cancer cells, ureteral cancer cells, urethral cancer cells, pharynx cancer cells, vaginal cancer cells, tonsil cancer cells, anal cancer cells, pleura cancer cells, thymic carcinoma cells, nasopharynx cancer cells, or cancer stem cells, but not limited thereto, and all the subjects suspected of having any kind of cancer may be included.

Herein, the term "fluidity" or "flowability" means flow, a motion or fluidity applied to a liquid medium, a biological sample, a diluted liquid medium, or a diluted biological sample, or applied to cells in a liquid medium, a biological sample, a diluted liquid medium, or a diluted biological sample, and specifically, means that a liquid medium, a biological sample, a diluted liquid medium or a diluted biological sample flows at a specific velocity, so that a cells in a liquid medium, a biological sample, a diluted liquid medium or a diluted biological sample have specific velocity. In one embodiment of the present invention, the fluidity or flowability of the liquid medium may be achieved by providing fluidity or flowability to a fixed liquid medium, or increasing velocity of a liquid medium having fluidity. The fluidity or flowability may be applied so that the liquid medium, the biological sample, the diluted liquid medium or the diluted biological sample has the velocity of 1 to 200 um/s, 1 to 150 um/s, 1 to 100 um/s, 1 to 90 um/s, 1 to 80 um/s, 1 to 70 um/s, 1 to 60 um/s, 1 to 50 um/s, 1 to 40 um/s, 1 to 39 um/s, 1 to 38 um/s, 1 to 37 um/s, 1 to 36 um/s, 1 to 35 um/s, 1 to 34 um/s, 1 to 33 um/s, 1 to 32 um/s, 1 to 31 um/s, 1 to 30 um/s, 5 to 200 um/s, 5 to 150 um/s, 5 to 100 um/s, 5 to 90 um/s, 5 to 80 um/s, 5 to 70 um/s, 5 to 60 um/s, 5 to 50 um/s, 5 to 40 um/s, 5 to 39 um/s, 5 to 38 um/s, 5 to 37 um/s, 5 to 36 um/s, 5 to 35 um/s, 5 to 34 um/s, 5 to 33 um/s, 5 to 32 um/s, 5 to 31 um/s, 5 to 30 um/s, 10 to 200 um/s, 10 to 150 um/s, 10 to 100 um/s, 10 to 90 um/s, 10 to 80 um/s, 10 to 70 um/s, 10 to 60 um/s, 10 to 50 um/s, 10 to 40 um/s, 10 to 39 um/s, 10 to 38 um/s, 10 to 37 um/s, 10 to 36 um/s, 10 to 35 um/s, 10 to 34 um/s, 10 to 33 um/s, 10 to 32 um/s, 10 to 31 um/s, or 10 to 30 um/s, and as one example, it may be applied so that the liquid medium, the biological sample, the diluted liquid medium or the diluted biological sample has the velocity of 10 to 30 um/s.

The fluidity or flowability may be applied to cells in the liquid medium, the biological sample, the diluted liquid medium or the diluted biological sample, so that the cells have velocity of 1 to 200 um/s, 1 to 150 um/s, 1 to 100 um/s, 1 to 90 um/s, 1 to 80 um/s, 1 to 70 um/s, 1 to 60 um/s, 1 to 50 um/s, 1 to 40 um/s, 1 to 39 um/s, 1 to 38 um/s, 1 to 37 um/s, 1 to 36 um/s, 1 to 35 um/s, 1 to 34 um/s, 1 to 33 um/s, 1 to 32 um/s, 1 to 31 um/s, 1 to 30 um/s, 5 to 200 um/s, 5 to 150 um/s, 5 to 100 um/s, 5 to 90 um/s, 5 to 80 um/s, 5 to 70 um/s, 5 to 60 um/s, 5 to 50 um/s, 5 to 40 um/s, 5 to 39 um/s, 5 to 38 um/s, 5 to 37 um/s, 5 to 36 um/s, 5 to 35 um/s, 5 to 34 um/s, 5 to 33 um/s, 5 to 32 um/s, 5 to 31 um/s, 5 to 30 um/s, 10 to 200 um/s, 10 to 150 um/s, 10 to 100 um/s, 10 to 90 um/s, 10 to 80 um/s, 10 to 70 um/s, 10 to 60 um/s, 10 to 50 um/s, 10 to 40 um/s, 10 to 39 um/s, 10 to 38 um/s, 10 to 37 um/s, 10 to 36 um/s, 10 to 35 um/s, 10 to 34 um/s, 10 to 33 um/s, 10 to 32 um/s, 10 to 31 um/s, or 10 to 30 um/s, and as one example, the fluidity or flowability may be applied to the cells so that the cells have the velocity of 10 to 30 um/s.

Herein, the term "micro-vibration" means motions less than a certain threshold of human recognizable motions, and for example, may mean small vibrations occurring while cancer cells move through a liquid medium. When cells move in a liquid medium, micro-vibration according to motions occurs, and cancer cells cause specific micro-vibration distinguished from normal cells when moving in a liquid medium. For example, cancer cells may cause micro-vibration having a frequency of 0.1 to 1.5 Hz, when moving in blood at a velocity of 10 to 30 um/s. When the micro-vibration is amplified and visualized, it may be visualized as a trajectory by cell motions.

The trajectory means motions of a liquid medium generated by motions of cells in a liquid medium. The trajectory may be visualized by the amplification. More specifically, the trajectory means motions of a liquid medium generated by micro-vibration of cells. However, the trajectory includes all changes to be visualized by frequency amplification so that micro-vibration which was not observed before frequency amplification becomes recognizable to human eyes. The trajectory may occur due to surface-specificity of cancer cells. The trajectory may mean a pixel of which brightness value is changed, or a set of pixels of which brightness value is changed, when comparing pixels at the same position at the same random moment, in the video of the moving cells, before and after frequency amplification of the video of moving cells, and for example, may be a pixel with an increased brightness value, a set of pixels with an increased brightness value, a pixel with an increased level of brightness, or a set of pixels with an increased level of brightness. The increase of the brightness value may mean a change which is an increase in a level of brightness of a pixel, a change which is a more increase in a brightness of a pixel, a change that a color value of a pixel becomes closer to white, or the like. The trajectory may move together with motions of the cells.

The pixel or set of pixels at the same position at the same random moment may be selected by one or more of pixels present in a specific region from pixels representing the cells in the video.

The specific region may be selected in pixels of which range is set up, down, left and right, as specific multiple times of the length of the maximum horizontal length or maximum vertical length of the set of pixels representing the cells, from pixels representing the cells in the video.

The specific region may be selected in pixels of which range is set up, down, left and right, as a specific multiple times of the length of the maximum horizontal length or maximum vertical length of the set of pixels representing the cells, from pixels at the up, down, left and right end of pixels representing the cells.

The specific multiple times may be 0.1 to 100 times, 0.1 to 90 times, 0.1 to 80 times, 0.1 to 70 times, 0.1 to 60 times, 0.1 to 50 times, 0.1 to 40 times, 0.1 to 30 times, 0.1 to 20 times, 0.1 to 10 times, 0.1 to 9 times, 0.1 to 8 times, 0.1 to 7 times, 0.1 to 6 times, 0.1 to 5 times, 0.1 to 4 times, 0.1 to 3 times, 0.1 to 2 times, 0.1 to 1 times, 0.1 to 0.9 times, 0.1 to 0.8 times, 0.1 to 0.7 times, 0.1 to 0.6 times, 0.1 to 0.5 times, 0.1 to 0.4 times, 0.1 to 0.3 times, 0.1 to 0.2 times, 0.5 to 100 times, 0.5 to 90 times, 0.5 to 80 times, 0.5 to 70 times, 0.5 to 60 times, 0.5 to 50 times, 0.5 to 40 times, 0.5 to 30 times, 0.5 to 20 times, 0.5 to 10 times, 0.5 to 9 times, 0.5 to 8 times, 0.5 to 7 times, 0.5 to 6 times, 0.5 to 5 times, 0.5 to 4 times, 0.5 to 3 times, 0.5 to 2 times, 0.5 to 1 time, 0.5 to 0.9 times, 0.5 to 0.8 times, 0.5 to 0.7 times, 0.5 to 0.6 times, 1 to 100 times, 1 to 90 times, 1 to 80 times, 1 to 70 times, 1 to 60 times, 1 to 50 times, 1 to 40 times, 1 to 30 times, 1 to 20 times, 1 to 10 times, 1 to 9 times, 1 to 8 times, 1 to 7 times, 1 to 6 times, 1 to 5 times, 1 to 4 times, 1 to 3 times, 1 to 2 times, or 1 to 1.5 times, but not limited thereto.

The pixels at the same position at the same random moment may be selected by pixels positioned at the opposite direction to the direction that the cells move, among pixels present in the specific region, from pixels representing the cells in the video.

According to one embodiment of the present invention, when amplifying the video of cells moving in a liquid medium in a certain frequency range to visualize micro-vibration of cells, and comparing pixels at the same position at the same random moment in the video of the moving cells before and after frequency amplification, if a pixel or a set of pixels of which brightness value is changed after the frequency amplification exists, the cells may be determined as cancer cells.

When the change of the brightness value of the pixel of the moving cells is larger than the change of the brightness value of the pixels of normal cells, when amplifying a video of normal cells moving in a liquid medium in the specific frequency range, the moving cells may be determined as cancer cells.

Herein, the term "frequency amplification" means amplifying a frequency of an image or a video, or the like, and for example, may mean amplifying a specific frequency in a video. Motions having various frequencies are present in a video, and a specific frequency of frequencies present in the video may be amplified by frequency amplification. According to one example of the present invention, the specific frequency range in the video may be amplified by a motion microscope.

The frequency to be amplified may be set to an appropriate range as desired, and for example, it may be a frequency of 0.001 to 10 Hz, 0.001 to 5 Hz, 0.001 to 4 Hz, 0.001 to 3 Hz, 0.001 to 2 Hz, 0.001 to 1.9 Hz, 0.001 to 1.8 Hz, 0.001 to 1.7 Hz, 0.001 to 1.6 Hz, 0.001 to 1.5 Hz, 0.001 to 1 Hz, 0.001 to 0.5 Hz, 0.01 to 10 Hz, 0.01 to 5 Hz, 0.01 to 4 Hz, 0.01 to 3 Hz, 0.01 to 2 Hz, 0.01 to 1.9 Hz, 0.01 to 1.8 Hz, 0.01 to 1.7 Hz, 0.01 to 1.6 Hz, 0.01 to 1.5 Hz, 0.01 to 1 Hz, 0.01 to 0.5 Hz, 0.1 to 10 Hz, 0.1 to 5 Hz, 0.1 to 4 Hz, 0.1 to 3 Hz, 0.1 to 2 Hz, 0.1 to 1.9 Hz, 0.1 to 1.8 Hz, 0.1 to 1.7 Hz, 0.1 to 1.6 Hz, 0.1 to 1.5 Hz, 0.1 to 1 Hz, 0.1 to 0.5 Hz, 0.5 to 10 Hz, 0.5 to 5 Hz, 0.5 to 4 Hz, 0.5 to 3 Hz, 0.5 to 2 Hz, 0.5 to 1.9 Hz, 0.5 to 1.8 Hz, 0.5 to 1.7 Hz, 0.5 to 1.6 Hz, 0.5 to 1.5 Hz, 0.5 to 1 Hz, 1 to 10 Hz, 1 to 5 Hz, 1 to 4 Hz, 1 to 3 Hz, 1 to 2 Hz, 1 to 1.9 Hz, 1 to 1.8 Hz, 1 to 1.7 Hz, 1 to 1.6 Hz, or 1 to 1.5 Hz, and as one example, it may be 0.1 to 1.5 Hz, but not limited thereto.

The amplification multiple of the frequency may be set to an appropriate range as desired, and for example, it may be amplified by over 1 to 100 times, over 1 to 90 times, over 1 to 80 times, over 1 to 70 times, over 1 to 60 times, over 1 to 50 times, over 1 to 40 times, over 1 to 35 times, over 1 to 30 times, over 1 to 29 times, over 1 to 28 times, over 1 to 27 times, over 1 to 26 times, over 1 to 25 times, over 1 to 24 times, over 1 to 23 times, over 1 to 22 times, over 1 to 21 times, over 1 to 20 times, over 1 to 15 times, over 1 to 10 times, over 1 to 5 times, 5 to 90 times, 5 to 80 times, 5 to 70 times, 5 to 60 times, 5 to 50 times, 5 to 40 times, 5 to 35 times, 5 to 30 times, 5 to 29 times, 5 to 28 times, 5 to 27 times, 5 to 26 times, 5 to 25 times, 5 to 24 times, 5 to 23 times, 5 to 22 times, 5 to 21 times, 5 to 20 times, 5 to 15 times, 5 to 10 times, 10 to 90 times, 10 to 80 times, 10 to 70 times, 10 to 60 times, 10 to 50 times, 10 to 40 times, 10 to 35 times, 10 to 30 times, 10 to 29 times, 10 to 28 times, 10 to 27 times, 10 to 26 times, 10 to 25 times, 10 to 24 times, 10 to 23 times, 10 to 22 times, 10 to 21 times, 10 to 20 times, 10 to 15 times, 15 to 90 times, 15 to 80 times, 15 to 70 times, 15 to 60 times, 15 to 50 times, 15 to 40 times, 15 to 35 times, 15 to 30 times, 15 to 29 times, 15 to 28 times, 15 to 27 times, 15 to 26 times, 15 to 25 times, 15 to 24 times, 15 to 23 times, 15 to 22 times, 15 to 21 times, or 15 to 20 times, and as one example, it may be amplified by 10 to 30 times, or 20 times, but not limited thereto.

Herein, the term "motion microscope" or "motion microscopy" is for amplifying small motions in a video, and is a technique to quantify small motions of a video, and then produce and visualize a new video that looks like to have large enough motions. According to one example of the present invention, the motion microscope may provide a video converted by amplifying a specific frequency, for example, a frequency of 0.1 to 1.5 Hz, from a video of moving cells in a liquid medium, a video in which cells with fluidity are filmed, a video of a biological sample with fluidity, or the like.

Herein, the motion microscope is a technique for visualizing and analyzing motions smaller than a threshold undetectable by human eyes. The motion microscope is a technique for visualizing and analyzing small motions, and a technique for quantifying small motions of a video and then producing a new video in which motions look large enough, to visualize it. In a digital camera, a number of pixels are present, and all minute vibrations undetectable by human eyes are recorded. The motion microscope provides a video of micro-vibration which was undetectable by human eyes, converted to be detectable by human eye. The motion microscope renders small motions again, and amplifies motions so as to be quantized for analysis, and then amplifies motions in a captured video sequence, and increases accuracy of amplification through noise analysis. When using the motion microscope, it is expected to be able to find out mechanics, power, dynamics, motions, or the like, which is hidden in various accumulations, and investigate unknown new phenomena.

According to one embodiment of the present invention, cancer cells seem to emit cancer cell-specific micro-vibration when moving in a liquid medium, and it is investigated that micro-vibration may be recognized as a form of trajectory when visualizing it. This is assumed as one by friction force occurring when cells move in a liquid medium, and it is assumed as because the size of cancer cells is bigger than normal cells, but not limited thereto. In addition, colorectal cancer cells and the like which have a size similar to normal cells can be distinguished from normal cells when visualizing micro-vibration, and this is assumed as because the surface of cancer cells are very rough than normal cells, but not limited thereto. Furthermore, by adjusting the velocity of a liquid medium, it can be seen that normal cells and cancer cells are distinguished more when visualized, and normal cells and cancer cells can be more clearly distinguished when the cells have fluidity at a velocity of 10 to 30 um/s. Considering this comprehensively, as the velocity of cells or liquid medium acts as an important factor for visualization of micro-vibration, but the friction force applied to cells is also assumed as an important variable, the velocity of cells or liquid medium may be set appropriately according to a used liquid medium, materials of a microfluidic channel, or the like, or as desired.

According to other one embodiment of the present invention, it relates to a cancer cell detection method, comprising a step of determining the cells as cancer cells, when micro-vibration having a frequency of 0.1 to 1.5 Hz occurs, when cells move in a liquid medium. Accordingly, one example of the present invention comprises applying fluidity to a liquid sample of a subject and amplifying a video of the liquid sample with fluidity by a frequency of 0.1 to 1.5 Hz to visualize it, and distinguishing cancer cells and normal cells according to the standard of motions (trajectory) of the liquid medium occurring by micro-vibration of the cells. In the step of amplifying the video to visualize micro-vibration of cells comprised in the liquid sample, cancer cells and normal cells have motions of the liquid medium occurring by micro-vibration of different cells. Cancer cells cause cancer cell-specific micro-vibration when moving, and have micro-vibration distinguished from normal cells.

The micro-vibration may be visualized by a motion microscope.

The liquid medium may be set to have specific velocity for the cells in the liquid medium to have the velocity of 10 to 30 um/s.

The velocity of the liquid medium may be 10 to 30 um/s.

The micro-vibration of the cells may be amplified by 10 to 30 times.

According to other one embodiment of the present invention, it relates to a method of detection of cancer cells, comprising a step of determining the cells as cancer cells, when the micro-vibration having a frequency of 0.1 to 1.5 Hz is visualized by amplification, in a video in which cells with fluidity are filmed.

The cells with fluidity may have a velocity of 10 to 30 um/s.

The cells with fluidity may move in a liquid medium at a velocity of 10 to 30 um/s.

The micro-vibration may be amplified by 10 to 30 times.

According to other one example of the present invention, a method of detecting cancer cells, comprising steps of treating frequency amplification to a video in which cells with fluidity are filmed; and determining the cells as cancer cells, when the frequency amplification occurs by the treatment, may be provided.

The cells with fluidity may have a velocity of 10 to 30 um/s.

The cells with fluidity may move in a liquid medium having a velocity of 10 to 30 um/s.

The frequency may be a frequency of 0.1 to 1.5 Hz.

The frequency amplification may be amplified by 10 to 30 times.

According to other one embodiment of the present invention, it relates to a method of determining cancer cells in a sample, comprising a step of amplifying a frequency of a video of a biological sample with fluidity.

The method of determining cancer cells in a sample may further comprise a step of analyzing the amplified video to determine cancer cells.

The step of determining may comprise a step of determining them as cancer cells, when the trajectory of cells is visualized by frequency amplification.

The step of determining may comprise a step of determining whether the trajectory occurs by the frequency amplification and determine them as cancer cells when the trajectory occurs.

The trajectory occurs by the motions of the cells, and it may be that micro-vibration which is not observed before frequency amplification is visualized so as to be made recognized by human eyes by frequency amplification.

The biological sample image with fluidity may comprise a movement video of at least one or more of normal cells and at least one or more of cells suspected as cancer cells, and the step of determining may determine the cells suspected as cancer cells as cancer cells, when the change of the brightness value of the trajectory occurring after the frequency amplification of the cells suspected as cancer cells is larger than the change of the brightness value of the trajectory occurring after the frequency amplification of the normal cells.

The step of determining may determine the cells suspected as cancer cells as cancer cells, when the change of the brightness value of the trajectory occurring after the frequency amplification of the cells suspected as cancer cells is larger by over 1 time, 1.1 times or more, 1.2 times or more, 1.3 times or more, 1.4 times or more, 1.5 times or more, 1.6 times or more, 1.7 times or more, 1.8 times or more, 1.9 times or more, 2 times or more, 2.1 times or more, 2.2 times or more, 2.3 times or more, 2.4 times or more, 2.5 times or more, 2.6 times or more, 2.7 times or more, 2.8 times or more, 2.9 times or more, 3 times or more, 3.1 times or more, 3.2 times or more, 3.3 times or more, 3.4 times or more, 3.5 times or more, 3.6 times or more, 3.7 times or more, 3.8 times or more, 3.9 times or more, or 4 times or more of the change of the brightness value of the trajectory occurring after the frequency amplification of the normal cells.

The step of determining may use artificial intelligence, and the artificial intelligence may comprise steps of progressing data study using a deep-learning algorithm for determining whether the frequency amplification occurs by the treatment; and determining whether the frequency amplification occurs by the treatment in the cells by the data study, and may perform the step of determining.

According to other one embodiment of the present invention, it relates to a method of diagnosing a cancer, comprising steps of amplifying a video in which a biological sample of a subject with fluidity in a specific frequency range to visualize micro-vibration of cells comprised in the sample; detecting cancer cells distinguished from normal cells according to the motion standard of the biological sample occurring by the micro-vibration of the cells; and diagnosing the subject as a cancer patient when the cancer cells are detected.

According to other one embodiment of the present invention, it relates to a method of diagnosing a cancer, comprising steps of applying fluidity of 10 to 30 um/s to blood of a patient; obtaining a video filming the blood of the patient with fluidity; amplifying the filmed video in a specific frequency range to visualize micro-vibration; distinguishing cancer cells and normal cells according to the standard of motions (trajectory) of a liquid medium occurring by micro-vibration of the cells by the visualization, to detect cancer cells; and diagnosing the patient as a cancer patient, when the cancer cells are detected.

The method of diagnosing a cancer may further comprise a step of administering an anticancer agent into the object or performing anticancer treatment.

When the object to be diagnosed is an object being suspicious as a cancer patient, whether or not to treat a cancer treatment, a selection for cancer treatment method or the like may be conducted, after being determined as a cancer patient.

In addition, when the object to be diagnosed is already a cancer patient or an object was already treated an anticancer treatment, ex post monitoring of cancer treatment can be conducted by the diagnosis method, and accordingly, whether or not to treat a cancer treatment, or cancer treatment method selection may be performed. In other words, the object may be a patient diagnosed as a cancer patient at least once or more in the past, and for monitoring of progress of cancer, prognosis, efficacy of anticancer treatment, or recurrence of cancer, or the like, the cancer diagnosis method according to one example of the present invention may be used.

According to other embodiment of the present invention, it relates to a method of cancer treatment, comprising steps of amplifying a video which represents blood of a patient with fluidity to visualize micro-vibration; detecting cancer cells having a motion trajectory by the visualization; diagnosing the patient as a cancer patient, when the cancer cells are detected; and administering an anticancer agent.

The anticancer agent may be an aqueous anticancer agent or a hydrophobic anticancer agent, and for example, the aqueous anticancer agent may be one or more kinds selected from the group consisting of doxorubicin, idarubicin, epirubicin, mitomycin C and irinotecan, and the hydrophobic anticancer agent may be one or more kinds selected from the group consisting of Docetaxel, cis-platin, camptothecin, paclitaxel, Tamoxifen, Anasterozole, Gleevec, 5-fluorouracil (5-FU), Floxuridine, Leuprolide, Flutamide, Zoledronate, Doxorubicin, Vincristine, Gemcitabine, Streptozotocin, Carboplatin, Topotecan, Belotecan, Irinotecan, Vinorelbine, hydroxyurea, Valrubicin, retinoic acids, Methotrexate, Meclorethamine, Chlorambucil, Busulfan, Doxifluridine, Vinblastin, Mitomycin, Prednisone, Testosterone, Mitoxantron, aspirin, salicylates, ibuprofen, naproxen, fenoprofen, indomethacin, phenylbutazone, cyclophosphamide, mechlorethamine, dexamethasone, prednisolone registered patent 10-1074026-3-, celecoxib, valdecoxib, nimesulide, cortisone and corticosteroid.

Advantageous Effects

The present invention can detect cancer cells at low cost without using antibodies, fluorescent materials or radioactive materials, and can improve the accuracy of judgement by providing auxiliary data, when judging cancer tissue through MRI or X-ray and the like. In addition, it can be helpful to detect invisible cancer tissue covered by dense tissue.

The present invention can predict the possibility of recurrence of cancer through cancer cell detection after cancer tissue removal surgery, and can help selection to suitably change anticancer agents in anticancer treatment. In addition, it can separate cancer cells sufficiently even at a magnification of 40 times, and can prepare a portable device for cancer cell detection in a small size, and the cost of cancer cell detection is low, and therefore it is expected to be supplied to countries with low GDP.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 1a is a photograph showing the flow of blood using a polydimethylsiloxane chip silicon microfluidic channel.

FIG. 1b is a photograph showing taking a video by enlarging the flow of blood in the polydimethylsiloxane chip silicon microfluidic channel.

FIG. 1c is a photograph showing the result of taking a video by enlarging the flow of blood in the polydimethylsiloxane chip silicon microfluidic channel.

FIG. 2a is a diagram showing selecting colors as a magnification type in a motion microscope program.

FIG. 2b is a diagram showing setting the frequency as an advanced item in a motion microscope program.

FIG. 2c is a diagram showing setting the amplification ratio in a motion microscope program.

FIG. 3 is a drawing showing the result of frequency amplification of an image of moving cancer cells with a motion microscope program.

FIG. 4a is a drawing showing the result of observation when flowing breast cancer cells (MCF-7) and blood cells at a flow velocity of 50 to 70 um/s.

FIG. 4b is a drawing showing the result of observation when flowing breast cancer cells (MCF-7) and blood cells at a flow velocity of 10 to 30 um/s.

FIG. 5 is a drawing showing the result of frequency amplification with a motion microscope when various cancer cells are mixed.

FIG. 6a is a drawing showing a process of generating a file to be used for an artificial intelligence program (Tensorflow object detection api) by separating soccer players and soccer balls from a soccer game video.

FIG. 6b is a drawing showing a process of generating a file to be used for an artificial intelligence program (Tensorflow object detection api) to separate blood cells and cancer cells, by utilizing a cancer cell-specific white trajectory.

FIG. 6c is a drawing showing a process of learning data generated in FIG. 6b by an artificial intelligence program (Tensorflow object detection api) using TFRecord and configuration pipelines (xxx.config).

FIG. 6d is a drawing showing the result of cancer cell separation using a learned artificial intelligence program (Tensorflow object detection api).

DETAILED DESCRIPTION OF THE EMBODIMENTS

Hereinafter, the present invention will be described in more detail by the following examples. However, these examples are intended to illustrate the present invention only, but the scope of the present invention is not limited by these examples.

Example 1: Observation of Micro-Vibration of Breast Cancer Cells

To minimize an interference phenomenon between cells, a polydimethylsiloxane chip silicon microfluidic channel (Microfit, South Korea) was used (FIG. 1a). After flowing breast cancer cells (MCF-7; Korean Cell Line Bank) at a flow velocity of 10 to 30 um/s, they were magnified 100 times and were filmed as a video (FIG. 1b). FIG. 1c represents the result of video photographing.

To amplify a specific frequency in the photographed video, the video was converted using a motion microscope. Specifically, after connecting to "playground" item on a motion microscope program (https://lambda.qrilab.com/site/) and uploading the video, "start magnify" was pressed and "color" was selected as "magnification type" (FIG. 2a). Then, in "Advanced" item, 0.5 to 1.5 Hz was set (FIG. 2b), and the amplification was set to 20 (FIG. 2c). After completing setting, the frequency of 0.5 to 1.5 Hz in the video was amplified by pressing magnify.

The observation result was shown in FIG. 3. As a result, a white tail was shown specifically in cancer cells, and the cancer cell-specific trajectory was observed. For reference, when amplifying to 1.5 to 2 Hz, the cancer cell-specific trajectory was not shown.

Example 2: Observation of Micro-Vibration at Various Velocities

To confirm whether the cancer cell-specific trajectory is affected by the flow velocity of cells, breast cancer cells (MCF-7) were flowed at a flow velocity of 10 um/s to 30 um/s, and 50 um/s to 70 um/s, respectively, in blood diluted 35 times with saline, and after photographing a video by the same method as Example 1-1, the frequency of 0.5 to 1.5 Hz in the photographed video was amplified.

As a result, an obvious and thick trajectory was observed at a flow velocity of 50 to 70 um/s. However, also in blood cells, a dim trajectory was observed at this flow velocity. However, when the flow velocity of cells was 10 to 30 um/s, the trajectory was not observed in blood cells, and the trajectory was observed only in breast cancer cells. The result was shown in FIG. 4a and FIG. 4b. FIG. 4a represents the observation result of flowing breast cancer cells (MCF-7) and blood cells at a flow velocity of 50 to 70 um/s. FIG. 4b represents the observation result of flowing breast cancer cells (MCF-7) and blood cells at a flow velocity of 10 to 30 um/s.

Example 3: Observation of Blood when Various Cancer Cells are Present

To confirm that detection of cancer cells is possible when various cancer cells are mixed, various cancer cells such as breast cancer cells (MDA-MB-231), pancreatic cancer cells (Capan-1), and colorectal cancer cells (NC1-H498) and the like were mixed to blood diluted 35 times with saline respectively. Blue Fluorescent Protein was transfected into breast cancer and pancreatic cancer cells, and Red Fluorescent Protein was transfected into colorectal cancer cells. After filming a video by the same method as Example 1-1 with visible light, when the fluorescent protein was shown during the observation with a fluorescent microscope, the frequency of 0.5 to 1.5 Hz in the photographed video was amplified. The result was shown in FIG. 5.

As a result, the trajectory was not observed in blood cells, but a white tail was observed in breast cancer cells (MDA-MB-231), pancreatic cancer (Capan-1), and colorectal cancer (NC1-H498). In particular, even though the size of colorectal cancer cells was very similar to blood cells, it could be distinguished from blood cells by a specific trajectory.

Considering that the specific white tail was began to be observed only when cancer cells moved and such a white tail was not observed when cancer cells were fixed, the cancer cell-specific trajectory was assumed that this was because micro-vibration occurred at a specific frequency of 0.5 to 1.5 Hz than normal blood cells when cancer cells moved. This was assumed that this was because the surface of cancer cells was very rough than normal cells.

Thus, when the flow velocity of cells was 10 to 30 um/s, various cancer cells could be distinguished, and cancer cells having a similar size to blood cells could be distinguished. In other words, this means that cancer cells which are covered by blood cells and are not easy to be detected can be detected through analysis of micro-vibration.

In addition, the flow velocity of cells acts as an important factor, but the friction force acting on cells is assumed as an important variable, and therefore the adjustment of the flow velocity seems to be needed according to solutions to be used, and microfluidic channel materials. However, there was certainly a section of the flow velocity that could distinguish only cancer cells from blood cells.

Example 4: Observation of Cancer Cells in Blood Utilizing Artificial Intelligence Since a frequency of about 1 circulating tumor cell per $10^5 \sim 10^7$ white blood cells in actual blood, even though a specific trajectory occurs in cancer cells, it is difficult to observe it by naked eyes. To solve this, whether cancer cells in blood could be detected by applying an artificial intelligence program was confirmed.

Specifically, as the artificial intelligence program, Tensorflow object detection api was used (https://github.com/tensorflow/models/blob/master/research/object_detection/g3doc/inst allation.md). As input data, pixel position values of left top (x, y) and width, height, or left top (xmin, ymin) and right bottom (xmax, ymax), of Bounding Box surrounding a subject, were labelled by subject together with the class of the corresponding subject, and were written to an annotation file or were produced using LabelImg program. For example, a file can be produced by separating soccer players and soccer balls in a soccer game video, and the process was shown in FIG. 6a. By the same method, utilizing a cancer cell-specific white trajectory, an artificial intelligence program was trained so as to differentiate blood cells and cancer cells. FIG. 6b represents training an artificial intelligence program so as to differentiate blood cells and cancer cells, utilizing the cancer cell-specific white trajectory.

A model was trained using input data (TFRecord) and configuration pipelines (xxx.config). The process was shown in FIG. 6c.

The result of cell differentiation using Tensorflow object detection api was shown in FIG. 6d. It could be seen that cancer cells (NC1-H498) were recognized as red and normal blood cells were recognized as green.

In the present description, for contents which those skilled in the art of the present invention can sufficiently recognize and infer, details thereof were omitted, and in addition to specific examples described herein, more various modifications may be made in a range without departing from the technical spirit or essential components of the present invention. Accordingly, the present invention may be practiced otherwise than as specifically described and illustrated herein, and this can be understood by those skilled in the art of the present invention.

The invention claimed is:

1. A method of detecting cancer cells, comprising steps of:
preparing a video of cells moving at a velocity of 10 to 30 µm/s in a liquid medium,
visualizing micro-vibrations of the cells by amplifying the video in a specific frequency range, and
determining the cells as cancer cells when the cells have having a motion trajectory formed by the micro-vibrations.

2. The method of detecting cancer cells according to claim 1, wherein the frequency range is 0.1 to 1.5 Hz.

3. The method of detecting cancer cells according to claim 1, wherein amplifying the video in a specific frequency range is performed by a motion microscope.

4. The method of detecting cancer cells according to claim 1, wherein the micro-vibrations of cells are amplified by 10 to 30 times.

5. The method of detecting cancer cells according to claim 1, wherein the liquid medium is a biological liquid medium.

6. The method of detecting cancer cells according to claim 5, wherein the biological liquid medium is separated from a subject.

7. The method of detecting cancer cells according to claim 6, wherein the subject is one or more kinds selected from the group consisting of rodents, mice, rats, hamsters, guinea pigs, reptiles, amphibians, mammals, dogs, cats, pigs, cattle, sheep, monkeys, primates, mammals other than humans, primates other than humans and humans.

8. The method of detecting cancer cells according to claim 6, wherein the subject is a subject suspected of suffering from cancer.

9. The method of detecting cancer cells according to claim 6, wherein the subject is a subject suspected of having one or more kinds selected from the group consisting of breast cancer, colorectal cancer, pancreatic cancer, ovarian cancer, liver cancer, brain cancer, prostate cancer, lung cancer, gastric cancer, skin cancer, oral cancer, rectal cancer, laryngeal cancer, thyroid cancer, parathyroid cancer, colon cancer, bladder cancer, peritoneal carcinoma, adrenal cancer, tongue cancer, small intestine cancer, esophageal cancer, renal pelvis cancer, renal cancer, heart cancer, duodenal cancer, ureteral cancer, urethral cancer, pharyngeal cancer, vaginal cancer, tonsil cancer, anal cancer, pleura cancer, thymic carcinoma, nasopharyngeal cancer and cancer stem cells.

10. The method of detecting cancer cells according to claim 5, wherein the biological liquid medium is one or more kinds selected from the group consisting of blood, plasma, serum, body fluid, urine, mucus, saliva, lymph fluid, respiratory secretion, spinal fluid, brain spinal fluid, phlegm, sweat, vaginal mucus, sperm, amniotic fluid, amnion fluid, synovia, tissue lavage fluid, tears and nasal mucus.

11. The method of detecting cancer cells according to claim 10, wherein the method is applied to the blood sample, after it is diluted with saline in a volume ratio of more than 1 to 100 times.

12. The method of detecting cancer cells according to claim 1, wherein the cancer cell is one or more kinds selected from the group consisting of breast cancer cells, colorectal cancer cells, pancreatic cancer cells, ovarian cancer cells, liver cancer cells, brain cancer cells, prostate cancer cells, lung cancer cells, gastric cancer cells, skin cancer cells, oral cancer cells, rectal cancer cells, laryngeal cancer cells, thyroid cancer cells, parathyroid cancer cells, colon cancer cells, bladder cancer cells, peritoneal carcinoma cells, adrenal cancer cells, tongue cancer cells, small intestine cancer cells, esophageal cancer cells, renal pelvis cancer cells, renal cancer cells, heart cancer cells, duodenal cancer cells, ureteral cancer cells, urethral cancer cells, pharynx cancer cells, vaginal cancer cells, tonsil cancer cells, anal cancer cells, pleura cancer cells, thymic carcinoma cells, nasopharynx cancer cells, and cancer stem cells.

13. A method of visualizing micro-vibrations of cancer cells, comprising
visualizing micro-vibrations of cells by amplifying a video of cells moving in a liquid medium in a specific frequency range,
wherein the cancer cells generate micro-vibrations distinguished from normal cells when moving at a velocity of 10 to 30 µm/s in the liquid medium.

14. The method of visualizing micro-vibrations of cancer cells according to claim 13, wherein the specific frequency range is 0.1 to 1.5 Hz.

15. The method of visualizing micro-vibrations of cancer cells according to claim 13, wherein the cancer cells move at a velocity of 10 to 30 um/s.

16. The method of visualizing micro-vibrations of cancer cells according to claim 13, wherein the liquid medium is one or more kinds selected from the group consisting of blood, plasma, serum, body fluid, urine, mucus, saliva, lymph fluid, respiratory secretion, spinal fluid, brain spinal fluid, phlegm, sweat, vaginal mucus, sperm, amniotic fluid, amnion fluid, synovia, tissue lavage fluid, tears and nasal mucus.

17. A method of diagnosing a cancer, comprising
providing fluidity of a flow velocity of 10 to 30 um/s to a biological liquid sample of a subject;
obtaining a video of the sample having the fluidity;
visualizing micro-vibration of cells in the sample by amplifying the video in a frequency range of 0.1 to 1.5 Hz;
detecting cancer cells being distinguishable from normal cells, based on motion of the liquid sample caused by micro-vibration of the cells; and
determining the subject as a cancer patient, when the cancer cells are detected,
wherein the cancer cells generate micro-vibrations distinguished from normal cells when moving at velocity of 10 to 30 µm/s in the liquid medium.

18. The method according to claim 17, further comprising administering an anticancer agent to the subject.

19. The method according to claim 17, wherein the subject is a subject diagnosed with a cancer patient or a subject treated an anticancer treatment, and the method is used for monitoring of cancer progress, cancer prognosis, efficacy of anticancer treatment or recurrence of cancer.

* * * * *